US012589258B2

(12) United States Patent
Kamerling et al.

(10) Patent No.: US 12,589,258 B2
(45) Date of Patent: Mar. 31, 2026

(54) COMPUTER-IMPLEMENTED MEDICAL METHOD OF IRRADIATION (RT) TREATMENT PLANNING

(71) Applicant: Brainlab AG, Munich (DE)

(72) Inventors: Cornelis Kamerling, Munich (DE); Merle Schlottmann, Munich (DE); Svenja Lüngen, Munich (DE)

(73) Assignee: Brainlab SE, Munich (DE)

( * ) Notice: Subject to any disclaimer, the term of this patent is extended or adjusted under 35 U.S.C. 154(b) by 867 days.

(21) Appl. No.: 17/912,164

(22) PCT Filed: Sep. 17, 2021

(86) PCT No.: PCT/EP2021/075622
§ 371 (c)(1),
(2) Date: Sep. 16, 2022

(87) PCT Pub. No.: WO2023/041173
PCT Pub. Date: Mar. 23, 2023

(65) Prior Publication Data
US 2024/0207641 A1 Jun. 27, 2024
US 2025/0001207 A9 Jan. 2, 2025

(51) Int. Cl.
*A61N 5/10* (2006.01)
*G16H 20/40* (2018.01)
(52) U.S. Cl.
CPC ............. *A61N 5/103* (2013.01); *G16H 20/40* (2018.01)
(58) Field of Classification Search
None
See application file for complete search history.

(56) References Cited

U.S. PATENT DOCUMENTS

| | | | |
|---|---|---|---|
| 7,945,022 B2 * | 5/2011 | Nelms ................. | A61N 5/1071 |
| | | | 378/65 |
| 2017/0072221 A1 * | 3/2017 | Nord ..................... | G16H 20/40 |
| 2021/0138267 A1 | 5/2021 | Nord et al. | |

FOREIGN PATENT DOCUMENTS

| | | |
|---|---|---|
| JP | 2000-242722 A1 | 9/2000 |

OTHER PUBLICATIONS

International Search Report, Corresponding to PCT/EP2021/075622, filed Sep. 17, 2021, 12 pages.

* cited by examiner

*Primary Examiner* — Uzma Alam
*Assistant Examiner* — Djura Malevic
(74) *Attorney, Agent, or Firm* — Tucker Ellis LLP

(57) ABSTRACT

Provided is a computer-implemented medical method of irradiation treatment planning that includes an algorithm, which calculates irradiation treatment plans and at the same time considers the combination of the deliverability of the calculated RT plans, the relevancy of the calculated RT plans, and a reasonably distinctiveness between said calculated plans regarding their respective 3D dose distribution. The method automatically calculates and automatically preselects some of the calculated plans in steps S1 to S4, which can then be provided to the user. Moreover, in step S5 the method provides a beneficial way of automatically grouping together plans, such as by sorting the calculated and preselected plans. By visualizing these automatically calculated, pre-selected and grouped plans in a particular way to the user, the final plan selection by the user is facilitated in a fast, reliable and medically safe manner.

21 Claims, 5 Drawing Sheets

S1

1. Precompute x deliverable plans

S2 *

2. Find (local) trade-offs in dose domain

S3

3. Remove redundant plans

S4

4. Filter relevant plans

S5 *

5. Arrange plans by trade-off

S6 *

6. Generate graphical representation of trade-offs

S7

7. Plan selection by user

COMPUTER-IMPLEMENTED MEDICAL METHOD OF IRRADIATION (RT) TREATMENT PLANNING

RELATED APPLICATION DATA

This application is a national phase application of International Application No. PCT/EP2021/075622, filed Sep. 17, 2021, the contents of which are incorporated herein by reference.

FIELD OF THE INVENTION

The present invention relates to a computer-implemented medical method of irradiation treatment planning, a corresponding computer program, a non-transitory program storage medium storing such a computer program and a computer for executing the computer program, as well as a medical system comprising the aforementioned computer program and the aforementioned computer.

TECHNICAL BACKGROUND

For radiation treatment planning in the field of radiotherapy and/or radiosurgery, very sophisticated software programs are applied in order to find an appropriate or even the best radiation plan for the given medical and technical circumstances. In particular, such state of the art radiation treatment planning software solutions allow the medical practitioner to provide details about the following considerations to the software system.

Typically, a planning target volume (PTV) associated with or representing e.g. a metastasis is specified along with a desired prescribed dose. The prescribed dose should preferably be deposited in at least a partial volume, also referred to as coverage volume, of the planning target volume in order to ensure biological effectiveness of the irradiation treatment. Apart from that, one or more constraints to be fulfilled during irradiation treatment can be specified. Typically, an organ at risk (OAR) like e.g. an eye of the patient, which preferably is to be spared during irradiation treatment or which should not receive more than an allowed dose in at least a partial volume thereof, can be specified as constraint. An optimization is carried out, which takes into account the specified planning target volume, a desired dose value defined by the radiologist, the one or more constraints, usually the coverage volume of the planning target volume is determined and a corresponding irradiation treatment plan is generated. This is done by an optimization algorithm, a so called optimizer, in the software that is available since years. The irradiation treatment plan can then be utilized to carry out the actual irradiation treatment.

However, particularly for multiple brain metastases treatment planning the difficulty arises how to define the arc setup[MS1], which is then used by the gantry of the radiation treatment apparatus to carry out the irradiation of the patient. Such an arc setup comprises a plurality of arcs, each arc being defined by a combination of a patient table angle, a gantry start angle and a gantry stop angle. In other words, an arc setup defines a set of arc trajectories, wherein each trajectory is defined by a gantry start and gantry stop angle and a unique table angle. Prior art solutions of Brainlab AG are described in e.g. the documents WO 2015/039903 A1 and WO 2013/075743 A1.

One available software solution of Brainlab AG called "Multiple Brain Mets SRS" software is a treatment planning software that produces treatment plans consisting of dynamic conformal arcs (a treatment modality for linac-based radiation therapy in which the linac head rotates around a patient, utilizing a gantry) with a single iso-center as described in WO 2013/075743 A1. Fields are collimated dynamically using a multi-leaf collimator while the gantry of the linac rotates around the patient's head. The fields are shaped according to projections of the metastases for a finite set of gantry angles (control points). For each control point, a projected shape can be either opened or blocked to alter the dose contribution. Moreover, a negative or positive 2D margin can be added to the projected shape to influence the dose profile. Finally, monitor units (arc-weights) must be set per arc (single rotation of the gantry).[MS2][AO3]

Moreover, the prior art solution of Brainlab AG disclosed in WO 2021/058 112 A1 describes a computer-implemented medical method for radiation treatment (RT) planning for treating multiple brain metastases of a patient, in which the method acquires a first arc set up and then automatically suggests a second arc setup based on a result of a comparison of the first arc set up with given RT constraints.

However, as is known to the skilled reader, exploring trade-offs for stereotactic radiosurgery (SRS) treatment plans is nowadays still challenging. Re-optimizing after user interaction is slow and there is no obvious mapping between input optimizer parameters and dosimetric output parameters. At the same time, it can be assumed that for a given indication the number of trade-offs is limited.

The software solution of Brainlab AG "Cranial SRS and Spine SRS" previously included a dose-shaper functionality. The software allowed user interaction with an iso-dose line from an existing treatment plan. The change in iso-dose line was then translated into an optimizer objective. The goal was set to obtain a deliverable treatment plan such that the user change was incorporated into the plan. In practice, however, the dose-shaper did not work satisfactory, because changing the isodose line could only be used to locally decrease dose, and often the desired change could not be incorporated into the plan as the deliverability of desired change was either not achievable or the optimization goal could not be set. Further, reoptimization for a desired iso-dose line change took several minutes. This could not accommodate interactive user control over the dose distribution. Also, the dose-shaper could only be used for dose feature changes which can be represented by an iso-dose line change (e.g. it was not possible to remove hotspots, i.e. local high dose areas, in a target volume with such a tool). Moreover, the suggested freedom of the tool was typically counteracted by the rather strict SRS constraints. Finally, the dose-shaper was disbanded in version 3.0.

During their research, the inventors of the present invention have identified the need of improving the provision, particularly the automatic calculation, of irradiation treatment plans for the physician.

EXEMPLARY SHORT DESCRIPTION OF THE INVENTION

In the following, a short description of the specific features of the present invention is given, which shall not be understood to limit the invention only to the features or a combination of the features described in this section.

The disclosed method automatically calculates and automatically pre-selects some of the calculated plans in steps S1 to S4, which can then be suggested, i.e. provided to the user. Moreover, a beneficial way of automatically grouping together, i.e. sorting the calculated and pre-selected plans is presented in step S5. By visualizing these automatically calculated, pre-selected and grouped plans in a particular way to the user, the final plan selection by the user is facilitated in a fast, reliable and medically safe manner, as will be explained in more detail now.

The computer-implemented medical method of irradiation treatment planning suggested by the inventors of the present invention for the first time provides an algorithm, which calculates irradiation treatment plans and at the same time considers the combination of the deliverability of the calculated RT plans, the relevancy of the calculated RT plans, and a reasonably distinctiveness between said calculated plans regarding their respective 3D dose distribution.

In an embodiment, the presented method can also take into account that only a limited, explorable set of results of the calculated RT plans shall be provided to the user as a final result, as will be explained in more detail hereinafter.

Furthermore, a particular and very intuitive way of presenting these plans is provided by an embodiment of the present invention, which allows a precise and fast selection of the final plan that is ultimately used to irradiate the patient at a later point in time. As will be elucidated hereinafter in the context of particular embodiments, the grouped or sorted plans calculated by the method of the present invention can be provided to the user in a two-step visualization. First, the patient anatomy together with the one or more identified spatial dose differentiating regions (see step S2 described below in detail) are displayed together to the user. After receiving a user selection input, with which the user selects one of the identified spatial dose differentiating regions, those plans are simultaneously displayed, which were previously grouped together by the presented method for said identified spatial dose differentiating region, which was selected by the user. Particular, non-limiting embodiments thereof will be described in the context of FIGS. 3 and 4.

As will become apparent from the present disclosure, the plans are preferably displayed as respective 3D spatial dose distributions relative to the patient anatomy, i.e. as dose maps. According to this embodiment, the resulting plans are generated and displayed in the dose domain, and not as a histogram and not as DVH.[CK5] [AO6]In another embodiment, the resulting plans are generated and displayed in the dose domain and in addition, a histogram and/DVH are displayed as well to the user.

GENERAL DESCRIPTION OF THE INVENTION

In this section, a description of the general features of the present invention is given for example by referring to possible embodiments of the invention.

In general, the invention reaches the aforementioned object by providing, in a first aspect, computer-implemented medical method of irradiation treatment planning. The method comprises executing, on at least one processor of at least one computer (for example at least one computer being part of the medical system), the following exemplary steps:

calculating a plurality of deliverable irradiation treatment plans thereby considering at least one device constraint of a particular irradiation device (step S1);

identifying one or more spatial dose differentiating regions, in which a difference in spatial dose distribution exists between two or more of the calculated deliverable irradiation treatment plans (step S2);

comparing the calculated deliverable irradiation treatment plans regarding their respective spatial dose distribution and removing plans from the plurality of calculated deliverable irradiation treatment plans, which are considered to be redundant with respect to the spatial dose distribution (step S3);

filtering relevant plans out of the calculated plurality of deliverable irradiation treatment plans (step S4), wherein a plan is considered relevant if it is compliant with at least one given radiotherapy prescription of a patient and/or with one or more given radiotherapy constraints, and grouping those plans of the calculated deliverable irradiation treatment plans together, which provide a difference in the spatial dose distribution within a particular spatial region of the spatial dose distribution (step S5).

As will become apparent from this disclosure, the presented method allows generating a limited, but feasible for user exploration, set of treatment plans which are deliverable according to machine constraints, and are relevant, i.e. in line with the given radiotherapy prescription of a patient and/or with one or more given radiotherapy constraints. Moreover, the plans resulting from the method defined in steps S1-S5 are reasonably distinct, i.e. plans, which are considered equivalent with respect to their 3D dose distribution are considered redundant and are thus filtered, and removed from the finally provided set of plans that can be suggested/output to the user.

The inventors of the present invention were the first to find that an algorithm calculating irradiation treatment plans should at the same time consider the combination of deliverability of the calculated RT plans, relevancy of the calculated RT plans, and reasonably distinctiveness regarding their respective 3D dose distribution of the calculated RT plans. The presented method can also take into account that only a limited, explorable set of results of the calculated RT plans shall be provided to the user as a final result. Furthermore, a very intuitive way of presenting these plans is presented as well herein, which allows a precise and fast selection of the final plan that is ultimately used to irradiate the patient at a later point in time.

According to this method the steps S1-S4, as they are shown and explained in more detail in the context of e.g. FIG. 1, are carried out to finally "group" such calculated, deliverable, pre-selected and filtered plans together and assign them to one or more area of interests. These areas of interest are named "spatial dose differentiating regions" herein, since the area of interest is always defined by the existence of plans, which differ from each other in the 3D dose distribution. The present invention provides a solution to allow for interactive treatment plan interaction, potentially solving also all former dose-shaper problems, which were explained hereinbefore. Also this will be explained in more detail hereinafter.

The proposed method comprises five steps and can be performed for each new patient geometry for which a clinical treatment plan shall to be generated. The patient geometry is typically composed of at least 3D image data, typically a CT image, and a set of delineated 3D target volumes and risk structures. Thus, the presented method may use medical image data, in which body parts of the patient are segmented. Moreover, a template describing the prescription, i.e. clinical goals, and/or RT constraint shall be available, as will be explained in more detail hereinafter.

In the first step S1, a plurality of deliverable irradiation treatment plans are calculated, wherein this calculation considers at least one device constraint of a particular irradiation device. In other words, a precomputation of x deliverable plans is carried out. In this first step, the method generates a potentially large set of x deliverable plans, for example 10s, 100s, 1000s, based on e.g. a combination of several optimization parameters. Examples of such optimization parameters are e.g. discrete ranges of slider positions or tolerated volume entry values, as used by the skilled person in e.g. the Spine SRS software. Note that VMAT plans for Spine SRS can be analyzed, however, the method of the present invention can also be used with any arc or IMRT plan modality.

Furthermore, in step S2, one or more spatial dose differentiating regions are identified (in the respective plan), in which a difference in spatial dose distribution exists between two or more of the calculated deliverable irradiation treatment plans. In a particular embodiment explained hereinafter in detail, local trade-offs in the dose domain are identified. In particular embodiments described in more detail hereinafter, data analysis tools like e.g. principal component analysis or dose fusion can be used to compare all dose distributions of the plans calculated in step S1 among each other. Metrics, for example, distance to agreement, absolute dose difference, and/or deformation vector fields, can be used in particular embodiments to identify spatial regions where local and/or global dose changes are identified. Agreement is a distance metric for RT which combines dose and Euclidian distance, see the article "*A software tool for the quantitative evaluation of* 3*D dose calculation algorithms*", of William B. Harms Sr., Daniel A. Low, John W. Wong, James A. Purdysee, see https://aapm.onlinelibrary-.wiley.com/doi/abs/10.1118/1.598363.

In step S3, the calculated deliverable irradiation treatment plans are compared regarding their respective spatial dose distribution and redundant plans are removed from the plurality of calculated deliverable irradiation treatment plans, when a plan is considered to be redundant with respect to the spatial dose distribution of another calculated plan. Thus, this step describes the removal of redundant plans. For example, a metric can be used (as was described in detail hereinbefore), which detects duplicates. The presented method removes these accordingly. This may involve a sampling in the parameter space as established in step S2. The amount of redundancy may be determined algorithmically, but may also depend on user preferences. For example, allowing for a finer sampling potentially increases the number of plans to be explored by the user, but at the same time allows more fine-tuning of the dose distribution.

In step S4, relevant plans are filtered out of the calculated plurality of deliverable irradiation treatment plans. A plan is considered relevant if it is compliant with at least one given radiotherapy prescription of a patient and/or with one or more given radiotherapy constraints. Note that step S1 may have generated treatment plans, which would be considered none relevant by a physician. These plans shall be automatically removed from the final set of plans. The plans can for example be detected by automatically comparing them to a templated clinical protocol.

Regarding said step S4 and the "at least one given radiotherapy prescription" the following should be noted. The filtering step S4 ensures that the finally resulting plans of the method presented herein are generally acceptable for the physician, since the compliance with the given radiotherapy prescription-(s) of the individual patient and/or with the radiotherapy constraint(s) for said patient is checked. Hence, a pre-selection of medically relevant plans is carried for the physician in step S4.

In step S5, those plans of the calculated deliverable irradiation treatment plans are grouped together, which provide a difference in the spatial dose distribution within a particular spatial region of the spatial dose distribution. Said "spatial region" are also referred to hereinafter as "area of interest", since these are the areas, in which interesting dose differences occur, which the user might want to compare. As will be explained in more detail in the context of the figure descriptions, see e.g. FIGS. 3 and 4, the present invention thus allows displaying several areas of interest to a user in an image of the patient geometry/anatomy, and after receiving a user selection input of a particular area of interest, the different plans, which were automatically grouped together for this particular area of interest in step S5 are then simultaneously displayed to the user for his/her review.

Moreover, by means of step S5, i.e. grouping those plans of the calculated deliverable irradiation treatment plans together, which provide a difference in the spatial dose distribution within a particular spatial region of the spatial dose distribution, a meaningfully structuring of this limited set of feasible plans, is provided. These finally suggested plans can then be explored interactively and intuitively, in a reasonable amount of time, by a user using a graphical user interface, as will be elucidated hereinafter in more detail in the context of particular embodiments.

In particular embodiments, the method also comprises the calculation and provision of a graphical representation of identified spatial dose differentiating regions.

Generally, the identified spatial dose differentiating regions as characterized herein can be presented to the user by means of a graphical user interface (2D or 3D). According to particular embodiments of the present invention, the method also comprises a browsing functionality on a user interface, dose morphing and/or the application of heat maps for graphically displaying the results of steps S1 to S5, as will be explained in more detail hereinafter in the context of particular embodiments, see e.g. the embodiment of FIG. 3.

Note that the term "spatial dose distribution" as used herein can be considered and is understood by the skilled reader as a signal. This signal can be measured e.g. by a radiation detector, which is irradiated by the particular irradiation device and according to an irradiation treatment plan.

Moreover, the method of the present invention encompasses the use of one and alternatively the use of several radiotherapy prescriptions for said patient. For example, several radiotherapy prescriptions for several different target volumes within the patient can be used, which target volumes are to be irradiated during the RT treatment. However, the method can also be applied in situations where several radiotherapy prescriptions for a single target volume are used, wherein said single target volume is to be irradiated during the RT treatment according to said plurality of radiotherapy prescriptions.

In the context of the present invention the term "treatment plan" shall be understood as a set of control points each defined by a patient table angle, gantry angle, collimator angle and collimator leaf positions. Typically, they are optimized to reach a clinical goal/prescription and/or one or more constraints. As a result, a treatment plan also comprises a description of the resulting dose distribution at/within the patient's body.

Moreover, in the context of the present invention a plan is understood to be "deliverable" if it is represented by a valid set of control points, accepted by the control system of the linear accelerator (linac) for which it was generated. The deliverability of a plan can be verified by comparison with a list of machine constraints for all degrees of freedom.

Further, as is understood by the skilled reader, the term "relevant plan" as used herein is defined as a treatment plan, which has dosimetric properties close to the given clinical goals/constraints, and hence is relevant for user exploration/review by the user. [AO10] Thus, in the context of the present invention, a plan is considered relevant if it is compliant with at least one given radiotherapy prescription of a patient and/or with one or more given radiotherapy constraints.

In the context of the present invention, the term "redundant plan" shall be understood as a plan, which is dosimetrically considered a duplicate of another plan (from a user perspective). For example, a metric determining said similarity can be e.g. user defined, or pre-defined and can be a function of the 3D dose representation or a 2D dose representation, for example dose volume histogram (DVH). Thus, in the context of the present invention, a plan is considered redundant if said comparison of step S3 reveals that there is not at least a minimum difference between said plan and at least one other of said calculated deliverable irradiation treatment plans regarding their respective spatial dose distribution.

Moreover, if desired, the presented method can be limited in the number of feasible set of plans. For example, a pre-set threshold of maximum number of plans, e.g. 10 plans as maximum output number, can be set by the user and the method than limits the output provided to the user accordingly. This facilitates that the result of the presented method, i.e. the final set of calculated, pre-selected and filtered treatment plans can be explored by a user in a reasonable time (e.g. 10s instead of 10,000s).

Moreover, the presented method allows for indication specific planning. The method assumes there is contextual information on the geometry (anatomy, pathology, body part dependent) and clinical protocols (dose prescription standards, organ at risk limits, i.e. said given radiotherapy prescription of a patient/the one or more given radiotherapy constraints mentioned before) available. This limits the number of expected meaningful trade-offs.

Furthermore, the term "trade-off" as used herein is to be understood as defining a local quality indicator indicative for the quality of the result of an RT plan, or a property of a dose distribution, which can only be improved if another local quality indicator is impaired. Examples of quality indicators are the local maximum dose value, the dose line shape, the position of the isodose line relative to an organ at risk, and the dose gradient.

According to particular embodiments, a plan selection by the user and/or a feedback loop are comprised. This embodiment allows skipping, morphing, and/or other navigational operations between treatment plan representations in an interactive way, i.e. it is possible to assess multiple local dose distributions in seconds. A feedback loop may be provided if e.g. in step S4, too many plans have been generated for straightforward navigation.

For example, this feedback loop can involve user selection of a subset of treatment plans, which can then be further navigated in a recurrent step. The user can thereby add information, e.g. regarding trade-offs, and thus add the subjective level of treatment plan decision to the methodology. Such an interface can for example be realized in a virtual reality environment in which a user can interactively navigate through a 3D space showing patient geometry and the 3D dose distribution for each individual relevant plan or a subset of these plans. A sub-region of interest can for instance be represented by an ellipsoid or cloud shape.

When a graphical representation of the plans resulting from steps S1 to S5 are displayed to the user in step S6, the data representing the plans can for example be augmented with other global 1D and 2D quality indicators as are typically used clinically to quantify plan quality, like e.g. conformity index, gradient index, dose volume histograms.

In particular embodiments, the number of generated plans x is kept reasonable. As is appreciated by the skilled reader, the expected bottleneck of the method is the plan generation. By means of analyzing step S4 it is expected that a reasonable plan sampling from the user perspective can be established. If desired, a feedback loop can be incorporated, e.g. by learning from the user what plans are relevant and what not, e.g. by a voting option. Note that step S1 is expected to generate many plans which are removed in step S3. To keep the number of precomputed plans reasonable-, e.g. computable during a night or lunch break, a sampling algorithm shall be employed. This can be solved by evaluating a predetermined subset of the space. Alternatively, such an approach can be performed iteratively to reduce the number of required plans. Such an approach can e.g. be extended by incorporating user feedback of the finally selected plan. The number of plans can be reduced further by predicting an appropriate minimal set of sampled plans based on geometric properties of the patient anatomy, particularly geometric properties, e.g. distance between target volume and spinal cord.

According to an exemplary embodiment of the present invention, the method further comprises acquiring said given radiotherapy prescription of a patient. According to an exemplary embodiment of the present invention, the method further comprises acquiring said one or more given radiotherapy constraints. According to another exemplary embodiment, the method also comprises acquiring data about the patient anatomy.

The given radiotherapy prescription and/or the radiotherapy constraints and/or the patient anatomy can be provided in several different data formats. They can be gathered e.g. from a data storage device, like a server storing medical information about the RT for a particular patient. But the radiotherapy prescription and/or the radiotherapy constraints and/or the patient anatomy can also be provided by e.g. a user input via a respective interface of the medical system.

Note that the following steps S2, S3 and S4 can be carried out in the time sequence as shown in e.g. FIG. 1, but can alternatively also be carried out in any other different order, e.g. S3, S2, S4; or S3, S4, S2; or S2, S3, S4.

According to an exemplary embodiment of the present invention, the at least one device constraint defines whether an irradiation treatment plan is deliverable with said particular irradiation device.

As mentioned before, a plan is considered "deliverable" if it is represented by a valid set of control points, accepted by the control system of the linac for which it was generated. The deliverability of a plan can be verified by comparison with a list of machine constraints for all degrees of freedom.

According to an exemplary embodiment of the present invention, a plan is considered redundant if said comparison of step S3 reveals that there is not at least a minimum difference between said plan and at least one other of said calculated deliverable irradiation treatment plans regarding their respective spatial dose distribution.

In other words, a "redundant plan" shall be understood as a plan, which is dosimetrically considered a duplicate of another plan from a user perspective in a set of treatment plans as there is no relevant difference in clinical goals/constraints. As was described hereinbefore, metrics can be used for carrying out this comparison and for determining whether said minimum difference exists.

According to an exemplary embodiment of the present invention, the method comprises determining, for one or more of the calculated deliverable irradiation treatment plans, a respective degree of compliance of the calculated deliverable irradiation treatment plan to the at least one given radiotherapy prescription of a patient and/or one or more given radiotherapy constraints, and wherein a calculated deliverable irradiation treatment plan is considered compliant$_{[MS13]}$if the determined respective degree of compliance exceeds a given threshold$_{[AO14]}$.

Said threshold may be set by the user via a user input received by the respective software. However, said threshold may also be acquired or downloaded from a server storing medical data about the patient and/or statistical data about RT planning. As was described hereinbefore, metrics can be used for carrying out this comparison and for determining said compliance and whether the degree of compliance exceeds a given threshold.

According to an exemplary embodiment of the present invention, the calculated deliverable irradiation treatment plans are calculated/provided as a respective 3D spatial dose distribution relative to a patient anatomy/geometry, i.e. as dose maps.

According to this embodiment, the resulting plans are generated and displayed in the dose domain, and not as a histogram and not as DVH. Moreover, the patient anatomy/geometry is typically composed of at least 3D image data, typically a CT image, and a set of delineated 3D target volumes and risk structures. Thus, according an embodiment, the method comprises acquiring patient anatomy/geometry data, e.g. 3D image data and a set of delineated 3D target volumes and risk structures.

According to an exemplary embodiment of the present invention, the method further comprises the step of displaying a graphical representation of plans resulting from steps S1 to S5 to a user (step S6).

As can be easily retraced from the accompanying figures, a graphical representation of the calculated plans is what is shown to the user in order to allow for a comparison between potential plans, and for fine or final selection of the plan to be used later by an irradiation device. Preferably, dose maps are used.

According to an exemplary embodiment of the present invention, those plans, which were grouped together in step S5, are simultaneously displayed to a user as a respective 3D spatial dose distribution relative to the patient anatomy.

This embodiment ensures that the plans, which were grouped together and/or assigned to a particular "spatial dose differentiating region", are provided to the user at the same time such that he/she can do a plan comparison for said particular "spatial dose differentiating region". This can be easily retraced from e.g. FIGS. 3 and 4.

According to an exemplary embodiment of the present invention, the step S6 of displaying the graphical representation of plans resulting from steps S1 to S5 comprises the following steps:

displaying, to the user, in a first step (step S6a), the patient anatomy together with the one or more identified spatial dose differentiating regions, which are graphically highlighted to the user;

receiving a user selection input selecting one of the identified spatial dose differentiating regions (step S6b);

simultaneously displaying, in response to the received user input, those plans that were grouped together in step S5 for said identified spatial dose differentiating region, which was selected in step S6b, wherein the plans are displayed as respective 3D spatial dose distribution relative to the patient anatomy (step S6c).

As is apparent for the skilled reader, this embodiment generally defines two subsequent visualization steps, applied for example also in the specific embodiments shown in FIGS. 3 and 4 using heat maps and vector fields for intuitively displaying the identified spatial dose differentiating regions to the user. The user selects an "area of interest", i.e. spatial dose differentiating region, and the different treatment plans are displayed to the user separately, allowing for a fast comparison of said plans by the user. The user selection input may be received via e.g. a user interface of the computer/system carrying out the method of the present invention. Said computer/system may also receive a respective control signal, which corresponds to the user selection.

According to an exemplary embodiment of the present invention, the one or more of the identified spatial dose differentiating regions are displayed by means of a respective heat map.

As is known to the skilled reader, a heat map or heatmap is a data visualization technique that shows magnitude of a phenomenon as color in two dimensions or three dimensions. The variation in color may be by hue or intensity, giving obvious visual cues to the reader about how the phenomenon is clustered or varies over space. An example is shown in FIG. 3.

According to an exemplary embodiment of the present invention, the one or more of the identified spatial dose differentiating regions are displayed by means of a respective vector field.

In general, a vector field is understood as an assignment of a vector to each point in a subset of space. For example, a vector field in the plane can be visualised as a collection of arrows with a given magnitude and direction, each attached to a point in the plane. In a particular embodiment, the thickness of each arrow represents or indicates the range of treatment plan differences regarding their dose distribution. This can be easily retraced from the specific embodiment of FIG. 4.

According to an exemplary embodiment of the present invention, the graphical representation of plans resulting from steps S1 to S5 comprise one or more isodose lines, which are displayed to the user together with at least one planning target volume (PTV) and/or at least one organ at risk (OAR).

Two specific examples this embodiment are shown in the FIGS. 3 and 4. This embodiment entails displaying the OAR and the PTV to the user together with isodose lines, which are a result of the calculated plans provided via steps S1 to S5 as described hereinbefore. As was described before, typically, a planning target volume (PTV) associated with or representing e.g. a metastasis is specified along with a desired prescribed dose. The prescribed dose should preferably be deposited in at least a partial volume, also referred to as coverage volume, of the PTV in order to ensure biological effectiveness of the irradiation treatment. Furthermore, one or more constraints to be fulfilled during irradiation treatment can be specified. Typically, an organ at risk (OAR) like e.g. an eye of the patient, which preferably is to be spared during irradiation treatment or which should not receive more than an allowed dose in at least a partial volume thereof, can be specified as constraint.

According to an exemplary embodiment of the present invention, the given radiotherapy prescription of the patient and/or the one or more radiotherapy constraints define one or more of the following parameters: a coverage volume for a planning target volume (PTV) to be irradiated in an irradiation treatment with a prescribed dose; at least one constraint for an organ at risk (OAR); at least one delivery complexity parameter; and/or that the at least one constraint is indicative of an allowed dose deposited in at least a part of the organ at risk (OAR).

This embodiment provides examples of the previously introduced feature "given radiotherapy prescription of the patient and/or the one or more radiotherapy constraints".

The given radiotherapy prescription of the patient and/or the one or more radiotherapy constraints may contain one or more and/or may be defined by one or more delivery complexity parameters. One example of a delivery complexity parameter is the parameter describing how many and/or how extensive collimator leaf movements must be carried out to realize the RT treatment plan. In general, "delivery complexity parameter" as used herein can be embodied as e.g. a parameter that is indicative for the calculation limit or calculation boundary, or can be indicative for the irradiation device limit or irradiation device boundary. Said calculation limit or calculation boundary is understood by the skilled reader as the limit/boundary, beyond which the accuracy of the calculated RT plan compared to the irradiation and dose applied in reality is considered too low. This accuracy can be measured and checked with e.g. a phantom irradiation, where a radiation sensor is used to measure the actually delivered radiation and dose parameters. Moreover, the irradiation device limit or irradiation device boundary is understood by the skilled reader as the limit/boundary, beyond which the particular irradiation device is not able anymore to follow the calculated irradiation treatment plan, or simply cannot realize the irradiation as defined by the calculated irradiation treatment plan. For example, if too many and/or too extensive collimator leaf movements would have to be carried out to realize the plan, this can be an undue technical hurdle for the device.

According to an exemplary embodiment of the present invention, each calculated irradiation treatment plan comprises at least one, preferably a plurality of, irradiation arcs/beams, wherein each arc/beam is defined by a table angle (203), a gantry angle (204), a collimator angle, and collimator leaf positions.

Further, in the context of the present invention the term "control point" is defined by a combination of the following radiotherapy parameters: the gantry angle, the patient table angle, the positions of the leaves of the leaf collimator used to shape the radiation field, and the rotational position of the leaf collimator. It should also be noted that the application of leaf collimators in the field of radiotherapy is well known by the skilled person and it is exemplarily referred here to Brainlab AG's patent application WO 2013/075743 where its described in the context of FIGS. 3 and 4 how the leaves can be adjusted to target the target volume, i.e. one or more metastases.

[4017]
According to an exemplary embodiment of the present invention, the method further comprises the step of receiving a final irradiation plan selection input from a user and marking the corresponding calculated deliverable irradiation treatment plan as final plan to be used for carrying out the irradiation treatment with the irradiation device.

For example, the user may select one of the plans 308-310 or 408-410 displayed to the user in the non-limiting embodiments shown in FIGS. 3 and 4, if he/she wishes to select one of these plans as the plan, which shall ultimately be used for controlling the irradiation device for carrying out a medical procedure on the patient. An non-limiting example of a device carrying out such a medical procedure is shown in FIG. 2. Marking said plan can be carried out in several different ways, e.g. by naming the underlying data respectively.

According to an exemplary embodiment of the present invention, the step S2 of identifying one or more spatial dose differentiating regions comprises the step of identifying regions in the calculated deliverable irradiation treatment plans, which comprise at least one trade-off, wherein a trade-off is a quality indicator of and/or a property of the dose distribution of the respective deliverable irradiation treatment plan, which quality indicator/property of the dose distribution can only be improved if another quality indicator/property of the dose distribution is impaired.

According to an exemplary embodiment of the present invention, the quality indicator/property of the dose distribution is selected from the group comprising local maximum dose value, dose line shape, position of isodose line relative to organ at risk (OAR), and dose gradient.

If multiple trade-offs are identified in step S2, these can for example be grouped and/or sorted and/or indexed based on locality, dosimetric impact or other metrics. Depending on the trade-off to be explored, the grouping can help to conduct step 3 and 4. An example trade-off for a Spine SRS case could be the set of possible dose distributions in the region of interest where the spinal canal (typical dose limiting organ at risk) is closest to the vertebra to be treated.

According to another aspect of the present invention, a computer program is presented which, when running on a computer or when loaded onto a computer, causes the computer to perform the method steps of the method as presented herein. The computer program may be provided on a computer readable medium, on which the program is stored.

In this aspect, the invention is directed to a computer program which, when running on at least one processor (for example, a processor) of at least one computer (for example, a computer) or when loaded into at least one memory (for example, a memory) of at least one computer (for example, a computer), causes the at least one computer to perform the above-described method according to the first aspect. The invention may alternatively or additionally relate to a (physical, for example electrical, for example technically generated) signal wave, for example a digital signal wave, carrying information which represents the program, for example the aforementioned program, which for example comprises code means which are adapted to perform any or all of the steps of the method according to the first aspect. A computer program stored on a disc is a data file, and when the file is read out and transmitted it becomes a data stream for example in the form of a (physical, for example electrical, for example technically generated) signal. The signal can be implemented as the signal wave which is described herein. For example, the signal, for example the signal wave is constituted to be transmitted via a computer network, for example LAN, WLAN, WAN, for example the internet. The invention according to the second aspect therefore may alternatively or additionally relate to a data stream representative of the aforementioned program.

In a third aspect, the invention is directed to a non-transitory computer-readable program storage medium on which the program according to the fourth aspect is stored.

The computer program may be part of a computer program, but it can also be an entire program by itself. For example, the computer program element may be used to update an already existing computer program to get to the present invention.

The computer readable medium may be seen as a storage medium, such as for example, a USB stick, a CD, a DVD, a data storage device, a hard disk, or any other medium on which a program element as described above can be stored.

According to another aspect of the present invention, a computer is presented, which stores said computer program.

According to another aspect of the present invention, a medical system (200) is presented, which comprises the computer program and the at least one computer as presented hereinbefore.

According to an exemplary embodiment of the present invention, the medical system further comprises at least one electronic data storage device storing the at least one given radiotherapy prescription of the patient and/or the one or more given radiotherapy constraints; and the particular irradiation device for carrying out a medical procedure on the patient, wherein the at least one computer is operably coupled to the at least one electronic data storage device for acquiring, from the at least one data storage device, the at least one given radiotherapy prescription of the patient and/or the one or more given radiotherapy constraints, and the irradiation device for issuing a control signal to the irradiation device for controlling an operation of the irradiation device on the basis of one of the calculated deliverable irradiation treatment plans selected by a user.

According to an exemplary embodiment of the present invention, the irradiation device of said medical system comprises:

a treatment beam source (201) and a patient support unit (202), wherein the at least one computer is operably coupled to the irradiation device for issuing a control signal to the irradiation device for controlling, on the basis of the one calculated deliverable irradiation treatment plan selected by the user, at least one of an operation of the treatment beam source, and a position of the patient support unit.

Note that the invention does not involve or in particular comprise or encompass an invasive step, which would represent a substantial physical interference with the body requiring professional medical expertise to be carried out and entailing a substantial health risk even when carried out with the required professional care and expertise. For example, the invention does not comprise a step of positioning a medical implant in order to fasten it to an anatomical structure or a step of fastening the medical implant to the anatomical structure or a step of preparing the anatomical structure for having the medical implant fastened to it. More particularly, the invention does not involve or in particular comprise or encompass any surgical or therapeutic activity. The invention is instead directed as applicable to a computer-implemented medical method of irradiation treatment planning, which calculates potential RT plans that can be suggested, and indeed are suggested to the user. For this reason alone, no surgical or therapeutic activity, and in particular, no surgical or therapeutic step is necessitated or implied by carrying out the invention.

Definitions

Computer Implemented Method

The method in accordance with the invention is a computer implemented method. For example, all the steps or merely some of the steps (i.e. less than the total number of steps) of the method in accordance with the invention can be executed by a computer (for example, at least one computer). An embodiment of the computer implemented method is a use of the computer for performing a data processing method. An embodiment of the computer implemented method is a method concerning the operation of the computer such that the computer is operated to perform one, more or all steps of the method.

The computer for example comprises at least one processor and for example at least one memory in order to (technically) process the data, for example electronically and/or optically. The processor being for example made of a substance or composition which is a semiconductor, for example at least partly n- and/or p-doped semiconductor, for example at least one of II-, III-, IV-, V-, VI-semiconductor material, for example (doped) silicon and/or gallium arsenide. The calculating or determining steps described are for example performed by a computer. Determining steps or calculating steps are for example steps of determining data within the framework of the technical method, for example within the framework of a program. A computer is for example any kind of data processing device, for example electronic data processing device. A computer can be a device which is generally thought of as such, for example desktop PCs, notebooks, netbooks, etc., but can also be any programmable apparatus, such as for example a mobile phone or an embedded processor. A computer can for example comprise a system (network) of "sub-computers", wherein each sub-computer represents a computer in its own right. The term "computer" includes a cloud computer, for example a cloud server. The term "cloud computer" includes a cloud computer system which for example comprises a system of at least one cloud computer and for example a plurality of operatively interconnected cloud computers such as a server farm. Such a cloud computer is preferably connected to a wide area network such as the world wide web (WWW) and located in a so-called cloud of computers which are all connected to the world wide web. Such an infrastructure is used for "cloud computing", which describes computation, software, data access and storage services which do not require the end user to know the physical location and/or configuration of the computer delivering a specific service. For example, the term "cloud" is used in this respect as a metaphor for the Internet (world wide web). For example, the cloud provides computing infrastructure as a service (IaaS). The cloud computer can function as a virtual host for an operating system and/or data processing application which is used to execute the method of the invention. The cloud computer is for example an elastic compute cloud (EC2) as provided by Amazon Web Services™. A computer for example comprises interfaces in order to receive or output data and/or perform an analogue-to-digital conversion. The data are for example data which represent physical properties and/or which are generated from technical signals. The technical signals are for example generated by means of (technical) detection devices (such as for example devices for detecting marker devices) and/or (technical) analytical devices (such as for example devices for performing (medical) imaging methods), wherein the technical signals are for example electrical or optical signals. The technical signals for example represent the data received or outputted by the computer. The computer is preferably operatively coupled to a display device which allows information outputted by the computer to be displayed, for example to a user. One example of a display device is a virtual reality device or an augmented reality device (also referred to as virtual reality glasses or augmented reality glasses) which can be used as "goggles" for navigating. A specific example of such augmented reality glasses is Google Glass (a trademark of Google, Inc.). An augmented reality device or a virtual reality device can be used both to input information into the computer by user interaction and to display information outputted by the computer. Another example of a display device would be a standard computer monitor comprising for example a liquid crystal display operatively coupled to the computer for receiving display control data from the computer for generating signals used to display image information content on the display device. A specific embodiment of such a computer monitor is a digital lightbox. An example of such a digital lightbox is Buzz®, a product of Brainlab AG. The monitor may also be the monitor of a portable, for example handheld, device such as a smart phone or personal digital assistant or digital media player.

The invention also relates to a program which, when running on a computer, causes the computer to perform one or more or all of the method steps described herein and/or to a program storage medium on which the program is stored (in particular in a non-transitory form) and/or to a computer comprising said program storage medium and/or to a (physical, for example electrical, for example technically generated) signal wave, for example a digital signal wave, carrying information which represents the program, for example the aforementioned program, which for example comprises code means which are adapted to perform any or all of the method steps described herein.

Within the framework of the invention, computer program elements can be embodied by hardware and/or software (this includes firmware, resident software, micro-code, etc.). Within the framework of the invention, computer program elements can take the form of a computer program product which can be embodied by a computer-usable, for example computer-readable data storage medium comprising computer-usable, for example computer-readable program instructions, "code" or a "computer program" embodied in said data storage medium for use on or in connection with the instruction-executing system. Such a system can be a computer; a computer can be a data processing device comprising means for executing the computer program elements and/or the program in accordance with the invention, for example a data processing device comprising a digital processor (central processing unit or CPU) which executes the computer program elements, and optionally a volatile memory (for example a random access memory or RAM) for storing data used for and/or produced by executing the computer program elements. Within the framework of the present invention, a computer-usable, for example computer-readable data storage medium can be any data storage medium which can include, store, communicate, propagate or transport the program for use on or in connection with the instruction-executing system, apparatus or device. The computer-usable, for example computer-readable data storage medium can for example be, but is not limited to, an electronic, magnetic, optical, electromagnetic, infrared or semiconductor system, apparatus or device or a medium of propagation such as for example the Internet. The computer-usable or computer-readable data storage medium could even for example be paper or another suitable medium onto which the program is printed, since the program could be electronically captured, for example by optically scanning the paper or other suitable medium, and then compiled, interpreted or otherwise processed in a suitable manner. The data storage medium is preferably a non-volatile data storage medium. The computer program product and any software and/or hardware described here form the various means for performing the functions of the invention in the example embodiments. The computer and/or data processing device can for example include a guidance information device which includes means for outputting guidance information. The guidance information can be outputted, for example to a user, visually by a visual indicating means (for example, a monitor and/or a lamp) and/or acoustically by an acoustic indicating means (for example, a loudspeaker and/or a digital speech output device) and/or tactilely by a tactile indicating means (for example, a vibrating element or a vibration element incorporated into an instrument). For the purpose of this document, a computer is a technical computer which for example comprises technical, for example tangible components, for example mechanical and/or electronic components. Any device mentioned as such in this document is a technical and for example tangible device.

Acquiring Data

The expression "acquiring data" for example encompasses (within the framework of a computer implemented method) the scenario in which the data are determined by the computer implemented method or program. Determining data for example encompasses measuring physical quantities and transforming the measured values into data, for example digital data, and/or computing (and e.g. outputting) the data by means of a computer and for example within the framework of the method in accordance with the invention. The meaning of "acquiring data" also for example encompasses the scenario in which the data are received or retrieved by (e.g. input to) the computer implemented method or program, for example from another program, a previous method step or a data storage medium, for example for further processing by the computer implemented method or program. Generation of the data to be acquired may but need not be part of the method in accordance with the invention. The expression "acquiring data" can therefore also for example mean waiting to receive data and/or receiving the data. The received data can for example be inputted via an interface. The expression "acquiring data" can also mean that the computer implemented method or program performs steps in order to (actively) receive or retrieve the data from a data source, for instance a data storage medium (such as for example a ROM, RAM, database, hard drive, etc.), or via the interface (for instance, from another computer or a network). The data acquired by the disclosed method or device, respectively, may be acquired from a database located in a data storage device which is operably to a computer for data transfer between the database and the computer, for example from the database to the computer. The computer acquires the data for use as an input for steps of determining data. The determined data can be output again to the same or another database to be stored for later use. The database or database used for implementing the disclosed method can be located on network data storage device or a network server (for example, a cloud data storage device or a cloud server) or a local data storage device (such as a mass storage device operably connected to at least one computer executing the disclosed method). The data can be made "ready for use" by performing an additional step before the acquiring step. In accordance with this additional step, the data are generated in order to be acquired. The data are for example detected or captured (for example by an analytical device). Alternatively or additionally, the data are inputted in accordance with the additional step, for instance via interfaces. The data generated can for example be inputted (for instance into the computer). In accordance with the additional step (which precedes the acquiring step), the data can also be provided by performing the additional step of storing the data in a data storage medium (such as for example a ROM, RAM, CD and/or hard drive), such that they are ready for use within the framework of the method or program in accordance with the invention. The step of "acquiring data" can therefore also involve commanding a device to obtain and/or provide the data to be acquired. In particular, the acquiring step does not involve an invasive step which would represent a substantial physical interference with the body, requiring professional medical expertise to be carried out and entailing a substantial health risk even when carried out with the required professional care and expertise. In particular, the step of acquiring data, for example determining data, does not involve a surgical step and in particular does not involve a step of treating a human or animal body using surgery or therapy. In order to distinguish the different data used by the present method, the data are denoted (i.e. referred to) as "XY data" and the like and are defined in terms of the information which they describe, which is then preferably referred to as "XY information" and the like.

Treatment Beam

The present invention relates to the field of controlling a treatment beam. The treatment beam treats body parts which are to be treated and which are referred to in the following as "treatment body parts". These body parts are for example parts of a patient's body, i.e. anatomical body parts.

The present invention relates to the field of medicine and for example to the use of beams, such as radiation beams, to treat parts of a patient's body, which are therefore also referred to as treatment beams. A treatment beam treats body parts which are to be treated and which are referred to in the following as "treatment body parts". These body parts are for example parts of a patient's body, i.e. anatomical body parts. Ionising radiation is for example used for the purpose of treatment. For example, the treatment beam comprises or consists of ionising radiation. The ionising radiation comprises or consists of particles (for example, sub-atomic particles or ions) or electromagnetic waves which are energetic enough to detach electrons from atoms or molecules and so ionise them. Examples of such ionising radiation include x-rays, high-energy particles (high-energy particle beams) and/or ionising radiation emitted from a radioactive element. The treatment radiation, for example the treatment beam, is for example used in radiation therapy or radiotherapy, such as in the field of oncology. For treating cancer in particular, parts of the body comprising a pathological structure or tissue such as a tumour are treated using ionising radiation. The tumour is then an example of a treatment body part.

The treatment beam is preferably controlled such that it passes through the treatment body part. However, the treatment beam can have a negative effect on body parts outside the treatment body part. These body parts are referred to here as "outside body parts". Generally, a treatment beam has to pass through outside body parts in order to reach and so pass through the treatment body part.

Reference is also made in this respect to the following web pages: http://www.elekta.com/healthcare_us_elekta_vmat.php and http://www.varian.com/us/oncology/treatments/treatment_techniques/rapidarc.

Arrangement of Treatment Beams

A treatment body part can be treated by one or more treatment beams issued from one or more directions at one or more times. The treatment by means of the at least one treatment beam thus follows a particular spatial and temporal pattern. The term "beam arrangement" is then used to cover the spatial and temporal features of the treatment by means of the at least one treatment beam. The beam arrangement is an arrangement of at least one treatment beam.

The "beam positions" describe the positions of the treatment beams of the beam arrangement. The arrangement of beam positions is referred to as the positional arrangement. A beam position is preferably defined by the beam direction and additional information which allows a specific location, for example in three-dimensional space, to be assigned to the treatment beam, for example information about its co-ordinates in a defined co-ordinate system. The specific location is a point, preferably a point on a straight line. This line is then referred to as a "beam line" and extends in the beam direction, for example along the central axis of the treatment beam. The defined co-ordinate system is preferably defined relative to the treatment device or relative to at least a part of the patient's body. The positional arrangement comprises and for example consists of at least one beam position, for example a discrete set of beam positions (for example, two or more different beam positions), or a continuous multiplicity (manifold) of beam positions.

For example, one or more treatment beams adopt(s) the treatment beam position(s) defined by the positional arrangement simultaneously or sequentially during treatment (for example sequentially if there is only one beam source to emit a treatment beam). If there are several beam sources, it is also possible for at least a subset of the beam positions to be adopted simultaneously by treatment beams during the treatment. For example, one or more subsets of the treatment beams can adopt the beam positions of the positional arrangement in accordance with a predefined sequence. A subset of treatment beams comprises one or more treatment beams. The complete set of treatment beams which comprises one or more treatment beams which adopt(s) all the beam positions defined by the positional arrangement is then the beam arrangement.

BRIEF DESCRIPTION OF THE DRAWINGS

In the following, the invention is described with reference to the appended figures, which give background explanations and represent specific embodiments of the invention. The scope of the invention is however not limited to the specific features disclosed in the context of the figures, wherein.

DESCRIPTION OF EMBODIMENTS

Figure 1:
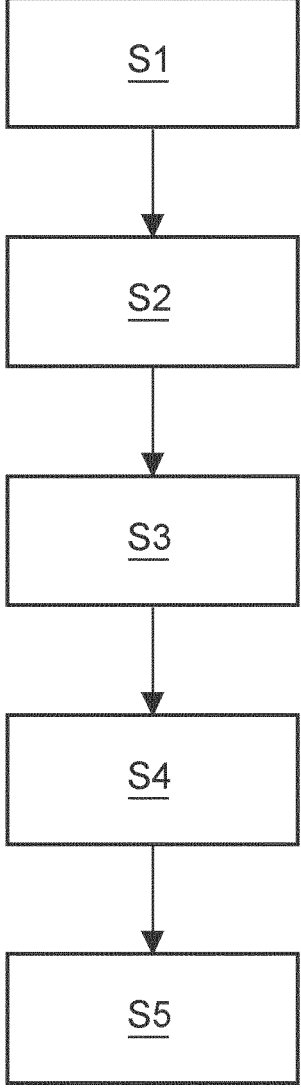
FIG. 1 illustrates a flow diagram of a computer-implemented medical method for radiation treatment (RT) planning according to an exemplary embodiment.

FIG. 1 shows a flow diagram of a computer-implemented medical method for radiation treatment (RT) planning comprising steps S1 to S5. Note that the following steps S2, S3 and S4 can be carried out in the time sequence as shown in FIG. 1, but can alternatively also be carried out in any other different order, e.g. S3, S2, S4; or S3, S4, S2; or S2, S3, S4. Furthermore, the proposed method of FIG. 1 can be performed for each new patient geometry for which a clinical treatment plan has to be generated. The patient geometry is typically composed of at least 3D image data, typically a CT image, and a set of delineated 3D target volumes and risk structures. Moreover, data, e.g. a template, describing the radiotherapy prescription of this individual patient and/or the one or more given radiotherapy constraints is provided.

As will be appreciated by the skilled reader, the method of FIG. 1 describes an algorithm calculating irradiation treatment plans, which at the same time considers the combination of the parameters deliverability of the calculated RT plans, relevancy of the calculated RT plans, and reasonably distinctiveness regarding their respective 3D dose distribution of the calculated RT plans. The method shown in FIG. 1 can also take into account that only a limited, explorable set of results of the calculated RT plans shall be provided to the user as a final result.

The computer-implemented medical method of irradiation treatment planning of FIG. 1 comprises as a first step S1 the calculation of a plurality of deliverable irradiation treatment plans thereby considering at least one device constraint of a particular irradiation device. Step S2 defines the identification of one or more spatial dose differentiating regions, in which a difference in spatial dose distribution exists between two or more of the calculated deliverable irradiation treatment plans. Moreover, in step S3 the calculated deliverable irradiation treatment plans are compared regarding their respective spatial dose distribution and plans are removed from the plurality of calculated deliverable irradiation treatment plans, which are considered to be redundant with respect to the spatial dose distribution. In step S4 relevant plans are filtered out of the calculated plurality of deliverable irradiation treatment plans. A plan is considered relevant if it is compliant with at least one given radiotherapy prescription of a patient and/or with one or more given radiotherapy constraints. Further, those plans of the calculated deliverable irradiation treatment plans are grouped together, which provide a difference in the spatial dose distribution within a particular spatial region of the spatial dose distribution.

Figure 2:
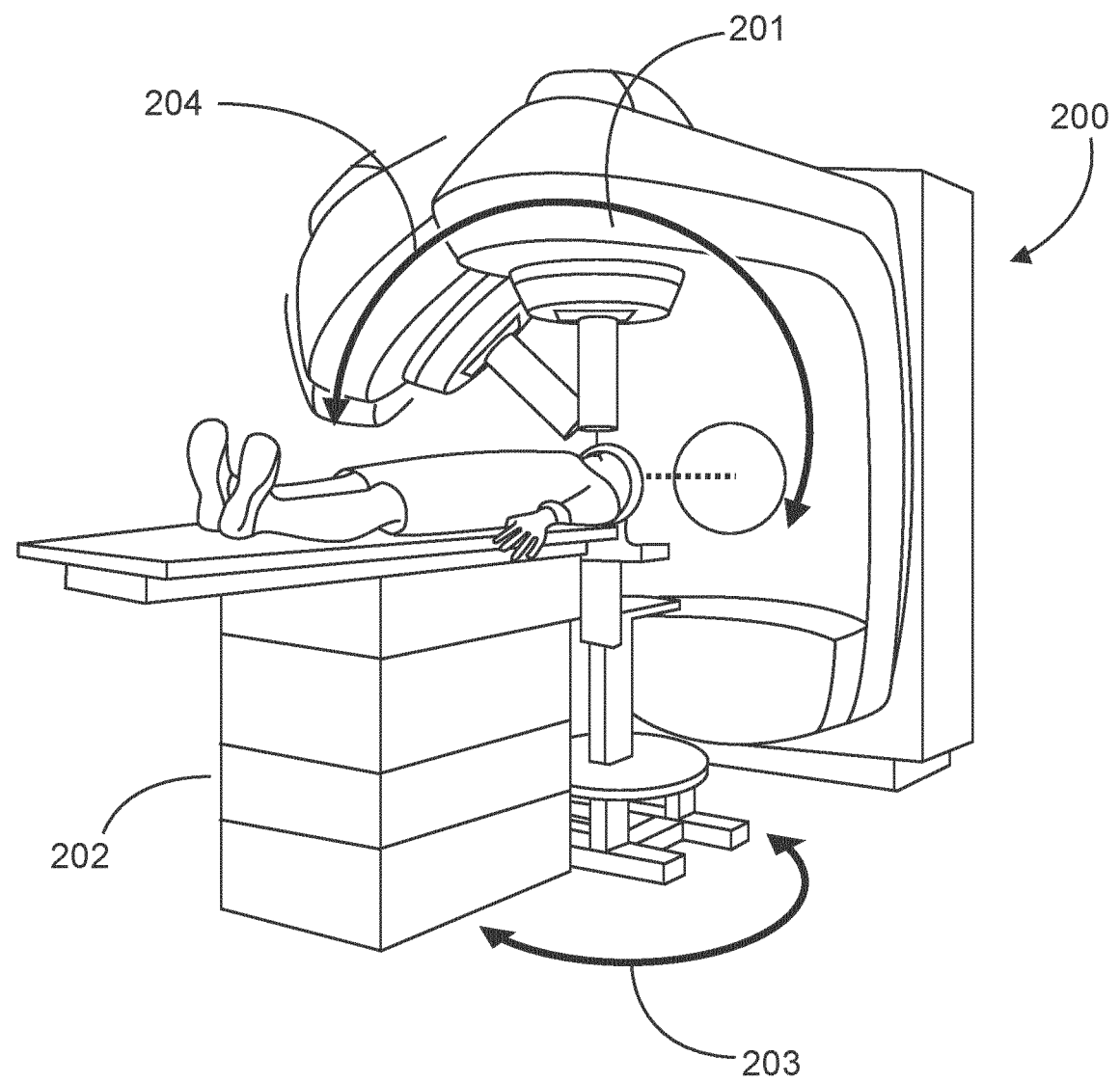
FIG. 2 schematically shows a medical system comprising an irradiation device for carrying out a medical procedure on the patient according to an exemplary embodiment of the present invention.

This method of FIG. 1 can be carried out by e.g. a processor, a computer or a medical system, as exemplarily shown in FIG. 2. After this automatic plan calculation and pre-selection, graphical representation of said plans resulting from steps S1 to S5 can be displayed to a user in step S6 (not shown). By visualizing these automatically calculated, pre-selected and grouped plans in a particular way to the user, the final plan selection by the user is facilitated in a fast, reliable and medically safe manner, as will be explained in more detail now. Preferably, the grouped or sorted plans calculated by the method of FIG. 1 can be provided to the user in a two-step visualization. First, the patient anatomy together with the one or more identified spatial dose differentiating regions (see step S2 described before in detail) are displayed together to the user. After receiving a user selection input, with which the user selects one of the identified spatial dose differentiating regions, those plans are simultaneously displayed, which were previously grouped together by the presented method for said identified spatial dose differentiating region, which was selected by the user. This will be explained in more detail in the context of FIGS. 3 and 4.

FIG. 2 schematically shows a medical system, which is embodied as a radiation treatment (RT) apparatus 200 according to an exemplary embodiment of the present invention. The RT apparatus 200 comprises a treatment beam source 201 and a patient support unit 202, which is embodied as a patient table 202. At least one computer is operably coupled to the RT apparatus for issuing a control signal to the radiation treatment apparatus for controlling, on the basis of one of the calculated deliverable irradiation treatment plans according to e.g. the method described in the context of FIG. 1, the operation of the treatment beam source 201 and/or the position of the patient support unit 202. In FIG. 2, the patient table angle is depicted by arrow 203 and the gantry angle is depicted by arrow 204. When the user has selected a final RT plan to be used for the medical treatment procedure, the system 200 can be controlled using said finally selected irradiation treatment plan.

In one embodiment of the medical system 200, the system comprises at least one electronic data storage device storing the at least one given radiotherapy prescription of the patient and/or the one or more given radiotherapy constraints. Said computer is operably coupled to the at least one electronic data storage device for acquiring, from the at least one data storage device, the at least one given radiotherapy prescription of the patient and/or the one or more given radiotherapy constraints. And the computer is coupled to the irradiation device for issuing a control signal to the irradiation device for controlling an operation of the irradiation device on the basis of one of the calculated deliverable irradiation treatment plan finally selected by a user. Moreover, the computer is operably coupled to the irradiation device for issuing a control signal to the irradiation device for controlling, on the basis of the one calculated deliverable irradiation treatment plan selected by the user, the operation of the treatment beam source (201) and/or the position of the patient support unit (202).

Figure 3:
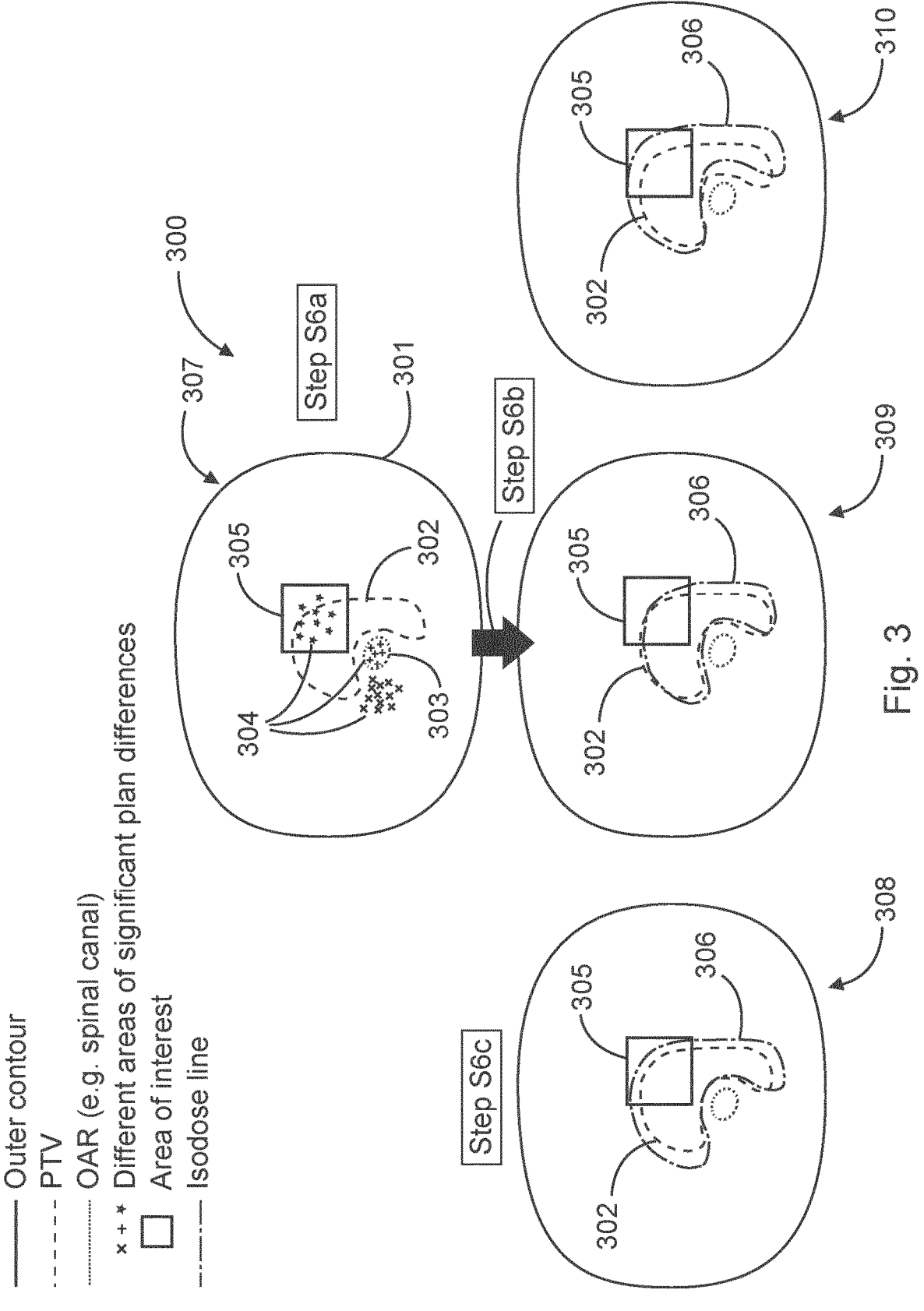
FIG. 3 schematically shows a visualization of multiple calculated, deliverable, relevant and non-redundant treatment plans in one graphical representation using heat maps according to an exemplary embodiment of the present invention.
Figure 4:
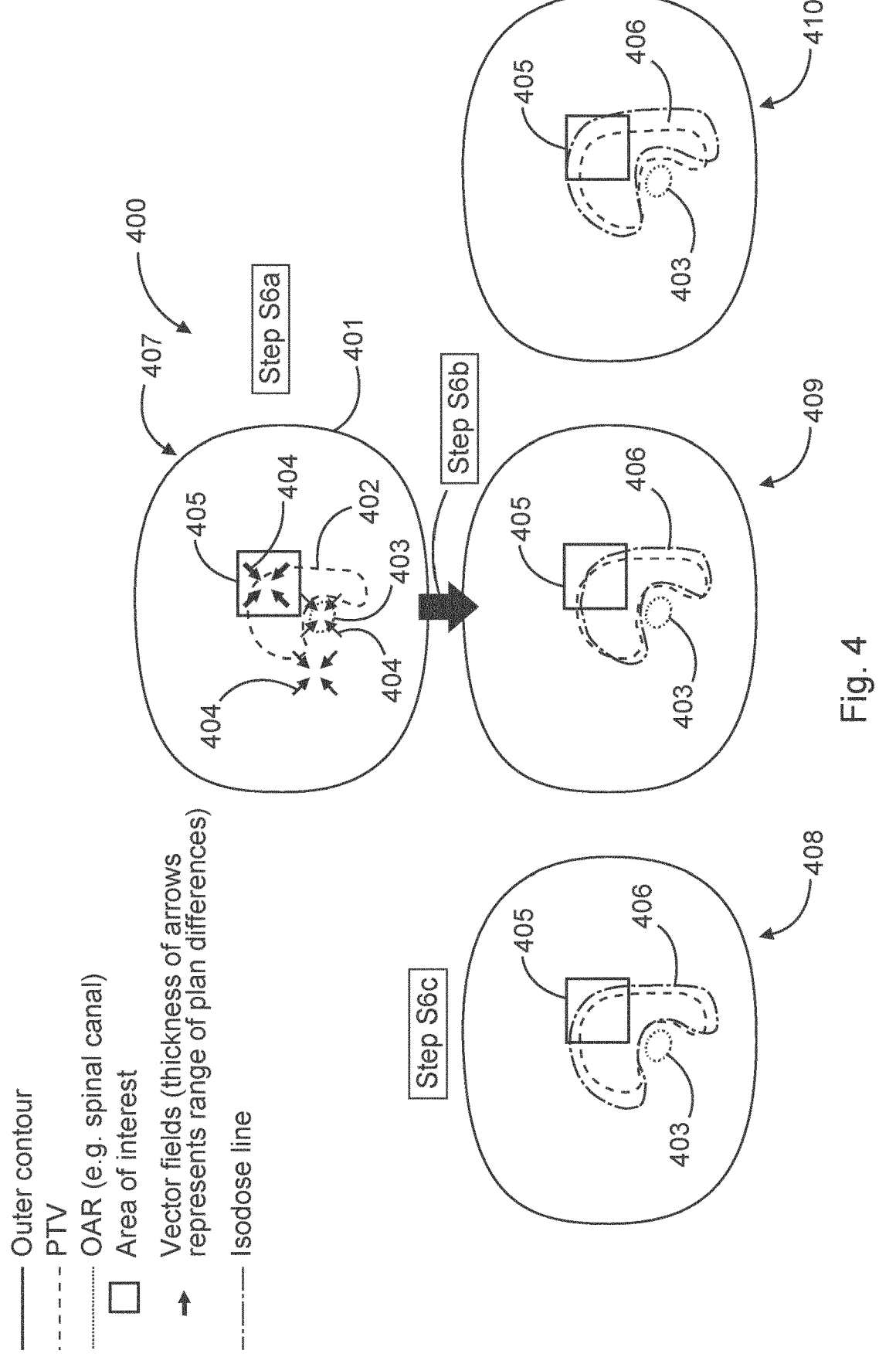
FIG. 4 schematically shows a visualization of multiple calculated, deliverable, relevant and non-redundant treatment plans in one graphical representation using vector fields according to an exemplary embodiment of the present invention.

Furthermore, FIGS. 3 and 4 provide a very intuitive way of presenting the resulting plans of steps S1 to S5 (see e.g. FIG. 1), which allows a precise and fast selection of the final plan that is ultimately to be used to irradiate the patient at a later point in time. In FIGS. 3 and 4, the calculated deliverable irradiation treatment plans are provided as a respective 3D spatial dose distribution relative to a patient anatomy/geometry, i.e. as dose maps. Thus, the resulting plans are generated and displayed in the dose domain, and not as a histogram and not as DVH In detail, FIG. 3 schematically shows a visualization 300 of multiple calculated, deliverable, relevant and non-redundant treatment plans 308, 309 and 310 in one graphical representation. In a first visualization step (step S6a), the patient anatomy together with the one or more identified spatial dose differentiating regions 304, which are graphically highlighted to the user, are displayed to the user, as is indicated by reference sign 307. This visualization comprises the outer contour 301, the planning target volume (PTV) 302, an organ at risk (OAR) 303, different areas of significant plan differences 304, and the area of interest 305. Further, in the next step (step S6b) a user selection input is received selecting one of the identified spatial dose differentiating regions 304, i.e. the area of interest. Moreover, in response to the received user input of step S6*b*, those plans that were grouped together in step S5 (see e.g. FIG. 1) for said identified spatial dose differentiating region, which was selected in step S6*b* by the user, are simultaneously displayed to the user (step S6*c*). As can be gathered from FIG. 3, the plans 308-310 are displayed as respective 3D spatial dose distribution, i.e. dose map, relative to the patient anatomy also showing the isodose line 306. While the embodiment of FIG. 3 uses heat maps, the embodiment of FIG. 4 uses vector fields.

In a similar way as FIG. 3, the embodiment of FIG. 4 schematically shows a visualization 400 of multiple calculated, deliverable, relevant and non-redundant treatment plans 408, 409 and 410 in one graphical representation. In a first visualization step (step S6*a*), the patient anatomy together with the one or more identified spatial dose differentiating regions 404, which are graphically highlighted to the user, are displayed to the user, as is indicated by reference sign 407. This visualization comprises the outer contour 401, the planning target volume (PTV) 402, an organ at risk (OAR) 403, different areas of significant plan differences 404, and the area of interest 405. Further, in the next step (step S6*b*) a user selection input is received selecting one of the identified spatial dose differentiating regions 404, i.e. the area of interest. Moreover, in response to the received user input of step S6*b*, those plans that were grouped together in step S5 (see e.g. FIG. 1) for said identified spatial dose differentiating region, which was selected in step S6*b* by the user, are simultaneously displayed to the user (step S6*c*). As can be gathered from FIG. 4, the plans 408-410 are displayed as respective 3D spatial dose distribution, i.e. dose map, relative to the patient anatomy also showing the isodose line 406.

Figure 5:
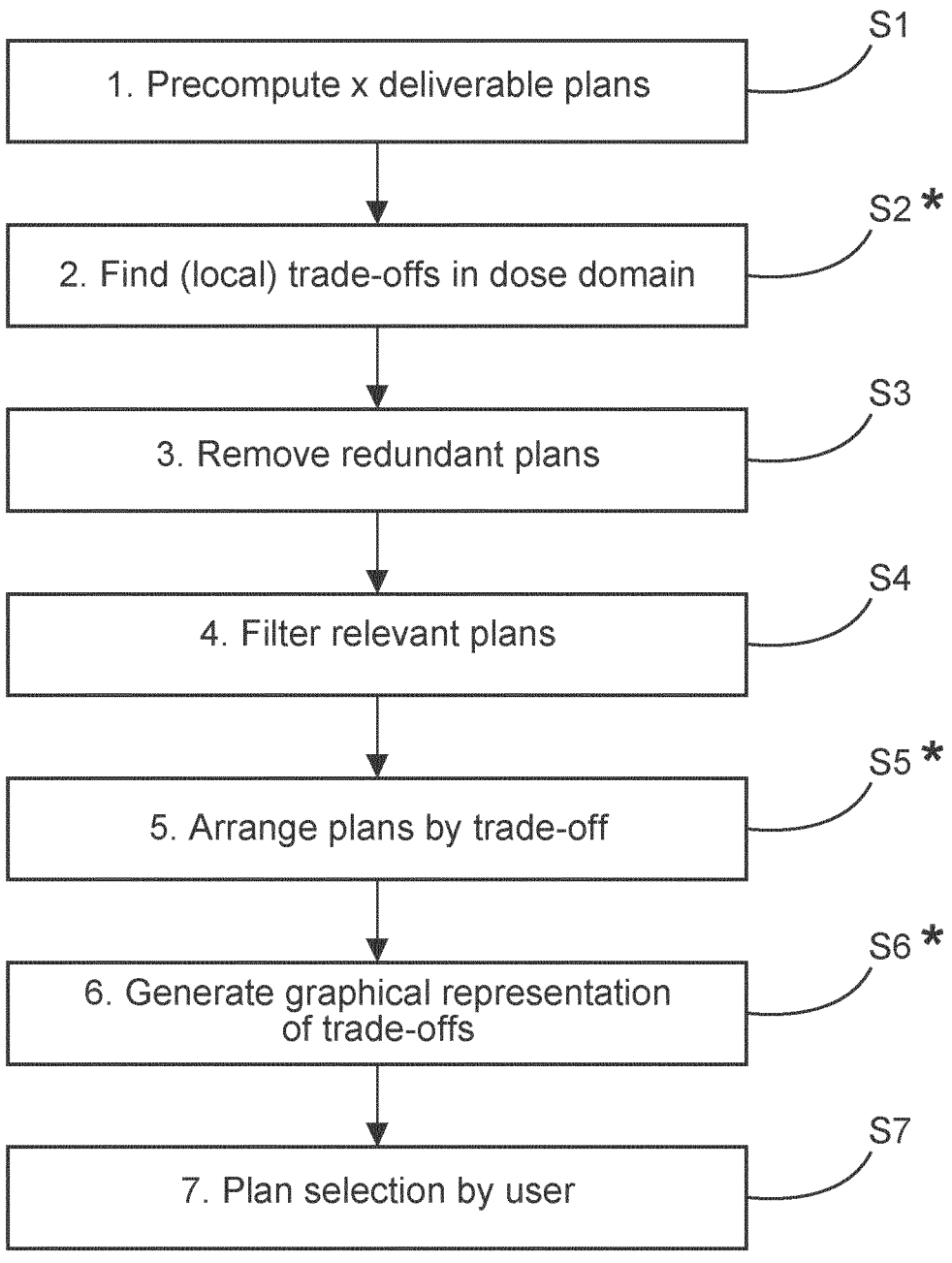
FIG. 5 illustrates a flow diagram of a computer-implemented medical method for radiation treatment (RT) planning according to an exemplary embodiment of the present invention.

FIG. 5 illustrates a flow diagram of a computer-implemented medical method for radiation treatment (RT) planning according to an exemplary embodiment of the present invention. The embodiment of FIG. 5 is a further development of the method of FIG. 1. In the embodiment of FIG. 5, the step S2 of identifying one or more spatial dose differentiating regions (as described hereinbefore in detail) comprises the step of identifying regions in the calculated deliverable irradiation treatment plans, which comprise at least one trade-off (step S2*). A trade-off is understood by the skilled reader as a quality indicator of and/or a property of the dose distribution of the respective deliverable irradiation treatment plan, which quality indicator/property of the dose distribution can only be improved if another quality indicator/property of the dose distribution is impaired. Preferably, the quality indicator/property of the dose distribution is selected from the group comprising local maximum dose value, dose line shape, position of isodose line relative to organ at risk (OAR), and dose gradient.

In steps S1 x deliverable plans are precomputed. As a first step, the method generates a (potentially large) set of x deliverable plans (for example 10s, 100s, 1000s) based on a combination of several optimization parameters (for example discrete ranges of slider positions or tolerated volume entry values in the Spine SRS software). For example, VMAT plans for Spine SRS can be analyzed, however, this method is also applicable to arc or IMRT plan modality. In step S2*, local trade-offs are found in the dose domain. Using data analysis tools (e.g. principal component analysis, dose fusion) all dose distributions are compared among each other. Metrics (for example, distance to agreement, absolute dose difference, deformation vector fields)

can be used to identify spatial regions where local and/or global dose changes are identified. In step S3 of FIG. 5 redundant plans are removed. A metric can be used (see above), which detects duplicates and removes these accordingly. This may involve a sampling in the parameter space as established in step S2*. The amount of redundancy may be determined algorithmically, but may also depend on user preferences (for example, allowing for a finer sampling potentially increases the number of plans to be explored by the user, but at the same time allows more fine-tuning of the dose distribution). In step S4 relevant plans are filtered. Step S1 may have generated treatment plans, which are not relevant. These shall be removed from the final set of plans. The plans can for example be detected by comparing to a templated clinical protocol. In step S5* the plans are arranged by trade-off. If multiple trade-offs are detected in step 2*, these shall for example be grouped and/or sorted and/or indexed based on locality, dosimetric impact or other metrics. Depending on the trade-off to be explored, the grouping can help to conduct step S3 and S4. An example trade-off for a Spine SRS case could be the set of possible dose distributions in the region of interest where the spinal canal (typical dose limiting organ at risk) is closest to the vertebra to be treated. In step S6* a graphical representation of the trade-offs is provided.

The trade-offs as characterized in the previous step shall be presented to the user by means of a graphical user interface (2D or 3D). Such an interface can for example include browsing functionality, dose morphing or heat maps. In step S7 the plan selection by the user and preferably a feedback loop are carried out. The tool as described in step S6* may allow skipping, morphing, or other navigational operations between treatment plan representations in an interactive way, i.e. it is possible to assess multiple (local) dose distributions in seconds. A feedback loop may be involved if e.g. in step 4, too many plans have been generated for straightforward navigation. For example, this feedback loop can involve user selection of a subset of treatment plans, which can then be further navigated in a recurrent step. The user can thereby add information regarding trade-offs and thus add the subjective level of treatment plan decision to the methodology. Such an interface can for example be realized in a virtual reality environment in which a user can interactively navigate through a 3D space showing patient geometry and a representation of local trade-offs (step 2) for each individual relevant plan or a subset of these plans. A subregion of interest can for instance be represented by an ellipsoid or cloud shape. The data representing trade-offs (step S6*) can for example be augmented with other (global) 1D and 2D quality indicators as are typically used clinically to quantify plan quality (e.g. conformity index, gradient index, dose volume histograms).

The invention claimed is:

1. A computer-implemented method of irradiation treatment planning, the method comprising:
   S1: calculating a plurality of deliverable irradiation treatment plans thereby considering at least one device constraint of a particular irradiation device;
   S2: identifying one or more spatial dose differentiating regions, in which a difference in spatial dose distribution exists between two or more of the calculated deliverable irradiation treatment plans;
   S3: comparing the calculated deliverable irradiation treatment plans regarding their respective spatial dose distribution and removing plans from the plurality of calculated deliverable irradiation treatment plans, which are considered to be redundant with respect to the spatial dose distribution;

S4: filtering relevant plans out of the calculated plurality of deliverable irradiation treatment plans, wherein a plan is considered relevant if it is compliant with at least one given radiotherapy prescription of a patient and/or with one or more given radiotherapy constraints; and S5: grouping those plans of the calculated deliverable irradiation treatment plans together, which provide a difference in the spatial dose distribution within a particular spatial region of the spatial dose distribution.

2. The method of claim 1, wherein the at least one device constraint defines whether an irradiation treatment plan is deliverable with said particular irradiation device.

3. The method according to claim 1, wherein a plan is considered redundant if said comparison of S3 reveals that there is not at least a minimum difference between said plan and at least one other of said calculated deliverable irradiation treatment plans regarding their respective spatial dose distribution.

4. The method according to claim 1, further comprising:
determining, for one or more of the calculated deliverable irradiation treatment plans, a respective degree of compliance of the calculated deliverable irradiation treatment plan to the at least one given radiotherapy prescription of a patient and/or one or more given radiotherapy constraints, and
wherein a calculated deliverable irradiation treatment plan is considered compliant if the determined respective degree of compliance exceeds a given threshold.

5. The method according to claim 1, wherein the calculated deliverable irradiation treatment plans are provided as a respective 3D spatial dose distribution relative to a patient anatomy.

6. The method according to claim 1, further comprising:
S6: displaying a graphical representation of plans resulting from S1 to S5 to a user.

7. The method according to claim 6, wherein those plans, which were grouped together in S5, are simultaneously displayed to the user as a respective 3D spatial dose distribution relative to a patient anatomy.

8. The method according to claim 7, wherein displaying the graphical representation of plans resulting from S1 to S5 in S6 comprises:
S6*a*: displaying, to the user, in a first (S6*a*), the patient anatomy together with the one or more identified spatial dose differentiating regions, which are graphically highlighted to the user;
S6*b*: receiving a user selection input selecting one of the identified spatial dose differentiating regions;
S6*c*: simultaneously displaying, in response to the received user input, those plans that were grouped together in S5 for said identified spatial dose differentiating region, which was selected in S6*b*, wherein the plans are displayed as the respective 3D spatial dose distribution relative to the patient anatomy.

9. The method according to claim 8, wherein one or more of the identified spatial dose differentiating regions are displayed by means of a respective heat map.

10. The method according to claim 8, wherein one or more of the identified spatial dose differentiating regions are displayed by means of a respective vector field.

11. The method according to claim 10, wherein a thickness of each arrow used in the vector field indicates a range of irradiation plan difference.

12. The method according to claim 6, wherein the graphical representation of plans resulting from S1 to S5 comprises one or more isodose lines, which are displayed to the user together with at least one planning target volume (PTV) and/or at least one organ at risk (OAR).

13. The method according to claim 1, wherein the given radiotherapy prescription of the patient and/or the one or more radiotherapy constraints define one or more of: a coverage volume for a planning target volume (PTV) to be irradiated in an irradiation treatment with a prescribed dose; at least one constraint for an organ at risk (OAR); at least one delivery complexity parameter; and/or that the at least one constraint is indicative of an allowed dose deposited in at least a part of the organ at risk (OAR).

14. The method according to claim 1, wherein each calculated irradiation treatment plan comprises at least one irradiation arc/beam, wherein each arc/beam is defined by a table angle, a gantry angle, a collimator angle, and collimator leaf positions.

15. The method according to claim 1, further comprising:
receiving a final irradiation plan selection input from a user and marking the corresponding calculated deliverable irradiation treatment plan as a final plan to be used for carrying out the irradiation treatment with the irradiation device.

16. The method according to claim 1, wherein identifying one or more spatial dose differentiating regions in S2 comprises identifying regions in the calculated deliverable irradiation treatment plans, which comprise at least one trade-off, wherein the at least one trade-off is a quality indicator of and/or a property of the dose distribution of the respective deliverable irradiation treatment plan, which quality indicator and/or property of the dose distribution is improved only if another quality indicator and/or property of the dose distribution is impaired.

17. The method according to claim 16, wherein the quality indicator and/or property of the dose distribution comprises a local maximum dose value, dose line shape, position of isodose line relative to organ at risk (OAR), and/or dose gradient.

18. A program logic stored in a memory device of a computer that when executed on the computer or when loaded onto the computer, causes the computer to perform a method of irradiation treatment planning, the method comprising:
S1: calculating a plurality of deliverable irradiation treatment plans thereby considering at least one device constraint of a particular irradiation device;
S2: identifying one or more spatial dose differentiating regions, in which a difference in spatial dose distribution exists between two or more of the calculated deliverable irradiation treatment plans;
S3: comparing the calculated deliverable irradiation treatment plans regarding their respective spatial dose distribution and removing plans from the plurality of calculated deliverable irradiation treatment plans, which are considered to be redundant with respect to the spatial dose distribution;
S4: filtering relevant plans out of the calculated plurality of deliverable irradiation treatment plans, wherein a plan is considered relevant if it is compliant with at least one given radiotherapy prescription of a patient and/or with one or more given radiotherapy constraints; and
S5: grouping those plans of the calculated deliverable irradiation treatment plans together, which provide a difference in the spatial dose distribution within a particular spatial region of the spatial dose distribution.

19. A medical system, comprising:

at least one computer operable to execute program logic stored in at least one electronic data storage device to perform a method of irradiation treatment planning comprising:

S1: calculating a plurality of deliverable irradiation treatment plans thereby considering at least one device constraint of a particular irradiation device;

S2: identifying one or more spatial dose differentiating regions, in which a difference in spatial dose distribution exists between two or more of the calculated deliverable irradiation treatment plans;

S3: comparing the calculated deliverable irradiation treatment plans regarding their respective spatial dose distribution and removing plans from the plurality of calculated deliverable irradiation treatment plans, which are considered to be redundant with respect to the spatial dose distribution;

S4: filtering relevant plans out of the calculated plurality of deliverable irradiation treatment plans, wherein a plan is considered relevant if it is compliant with at least one given radiotherapy prescription of the patient and/or with one or more given radiotherapy constraints; and S5: grouping those plans of the calculated deliverable irradiation treatment plans together, which provide a difference in the spatial dose distribution within a particular spatial region of the spatial dose distribution.

20. The medical system of claim 19, further comprising:

an irradiation device for carrying out a medical procedure on the patient, wherein the at least one electronic data storage device stores the at least one given radiotherapy prescription of the patient and/or the one or more given radiotherapy constraints, and wherein the at least one computer is operably coupled to:

the at least one electronic data storage device for acquiring, from the at least one electronic data storage device, the at least one given radiotherapy prescription of the patient and/or the one or more given radiotherapy constraints, and the irradiation device for issuing a control signal to the irradiation device for controlling an operation of the irradiation device based on one of the calculated deliverable irradiation treatment plans selected by a user.

21. The medical system according to claim 20, wherein the irradiation device comprises:

a treatment beam source and a patient support unit, wherein the at least one computer is operably coupled with the irradiation device for issuing a control signal to the irradiation device for controlling, based on the one calculated deliverable irradiation treatment plan selected by the user, at least one of:

an operation of the treatment beam source, and a position of the patient support unit.

* * * * *